United States Patent [19]

Seifert et al.

[11] 4,332,939

[45] Jun. 1, 1982

[54] PROCESS FOR THE PREPARATION OF FLUORINATED S-TRIAZINES

[75] Inventors: Gottfried Seifert, Muttenz; Sebastian Stäubli, Magden, both of Switzerland

[73] Assignee: Ciba-Geigy AG, Basel, Switzerland

[21] Appl. No.: 246,968

[22] Filed: Mar. 24, 1981

Related U.S. Application Data

[63] Continuation of Ser. No. 81,965, Oct. 4, 1979, abandoned, which is a continuation of Ser. No. 891,377, Mar. 29, 1978, abandoned.

[30] Foreign Application Priority Data

Apr. 6, 1977 [CH] Switzerland .......................... 4359/77
Apr. 15, 1977 [CH] Switzerland .......................... 4703/77

[51] Int. Cl.$^3$ ......................................... C07D 251/28
[52] U.S. Cl. .................................................. 544/217
[58] Field of Search ......................................... 594/217

[56] References Cited

FOREIGN PATENT DOCUMENTS 1044091 11/1958 Fed. Rep. of Germany .
 873251  7/1961 United Kingdom .
1273914  5/1972 United Kingdom .

OTHER PUBLICATIONS

Kwasnik, published in Klemm Inorganic Chemistry, vol. 1, pp. 239-244 (1948), published by the Office of Military Govt. for Germany.

*Primary Examiner*—John M. Ford
*Attorney, Agent, or Firm*—Edward McC. Roberts

[57] ABSTRACT

A process for the preparation of a fluorinated s-triazine, which comprises reacting a cyanuric halide, which contains at least one halogen other than fluorine, with hydrogen fluoride in the presence of active charcoal.

13 Claims, No Drawings

PROCESS FOR THE PREPARATION OF FLUORINATED S-TRIAZINES

This is a continuation of application Ser. No. 081,965 filed on Oct. 4, 1979, now abandoned, which in turn is a continuation of application Ser. No. 891,377 filed on Mar. 29, 1978, now abandoned.

The present invention relates to a process for the preparation of fluorinated s-triazines, which comprises reacting cyanuric halides, which contain at least one halogen other than fluorine, with hydrogen fluoride in the presence of active charcoal.

Cyanuric halides which contain at least one halogen other than fluorine and can be used for the process according to the invention are, for example: 2-fluoro-4,6-dichloro-s-triazine, 2,4-difluoro-6-chloro-s-triazine, 2-fluoro-4,6-dibromo-s-triazine, 2,4-difluoro-6-bromo-s-triazine, cyanuric bromide, cyanuric iodide and especially cyanuric chloride. In this context active charcoal is, as usual, to be understood as meaning amorphous carbon which has a very large number of pores and is distinguished by a large inner surface area (300 to 2,000 $m^2/g$). The active charcoal can be employed in powder form or, especially for the reaction in the gas phase, in the form of grains or tablets.

The reaction according to the invention can be carried out in a liquid mixture (if necessary in an autoclave at elevated temperature and under pressure), which contains the active charcoal in a finely divided form. Preferably, the reaction is carried out in the gas phase.

In a preferred embodiment of the process according to the invention, cyanuric chloride is reacted with hydrogen fluoride in the gas phase in the presence of active charcoal. With this reaction, the lower temperature limit depends on the excess of hydrogen fluoride used, at which the cyanuric chloride is still in the gas phase; for example for a molar ratio of hydrogen fluoride/cyanuric chloride of 4:1, the lower temperature limit is at 150° C. In order to obtain high yields of pure cyanuric fluoride, the reaction is advantageously carried out at temperatures between 150° and 300° C. The reaction is preferably carried out at between 180° and 220° C., since the highest yields of pure cyanuric fluoride are obtained within this temperature range. The lowest value of the molar ratio of hydrogen fluoride/cyanuric chloride at which cyanuric fluoride is still formed as the main product is about 3:1. Preferably, the reaction according to the invention is carried out at a molar ratio of hydrogen fluoride/cyanuric chloride of 3:1 to 10:1 and especially 4:1 to 5:1; values of the molar ratio of hydrogen fluoride/cyanuric chloride which are even higher than 10:1 likewise give very good yields of pure cyanuric fluoride.

If 2,4-difluoro-6-chloro-s-triazine or 2-fluoro-4,6-dichloro-s-triazine is used in place of cyanuric chloride as the starting material, very good yields of pure cyanuric fluoride are possible even with molar ratios of hydrogen fluoride/cyanuric halide which are lower than those mentioned above. For example, when 2,4-difluoro-6-chloro-s-triazine is used the reaction is advantageously carried out with a molar ratio of hydrogen fluoride/2,4-difluoro-6-chloro-s-triazine of 1:1 to 4:1, preferably about 2:1; if 2-fluoro-4,6-dichloro-s-triazine is used as the starting material, advantageous results are obtained with a molar ratio of hydrogen fluoride/2-fluoro-4,6-dichloro-s-triazine of 2:1 to 5:1 and preferably the reaction is carried out using a molar ratio of hydrogen fluoride/2-fluoro-4,6-dichloro-s-triazine of 3:1. When 2,4-difluoro-6-chloro-s-triazine or 2-fluoro-4,6-dichloro-s-triazine is used as the starting material, the reaction is also carried out at temperatures betwen 150° C. and 300° C.; preferably the reaction is carried out at between 180° C. and 220° C., as when cyanuric chloride is used as the starting material. Pure cyanuric fluoride is likewise obtaining in high yield when a mixture of 2,4-difluoro-6-chloro-s-triazine and 2-fluoro-4,6-dichloro-s-triazine or a mixture of cyanuric chloride, 2,4-difluoro-6-chloro-s-triazine and 2-fluoro-4,6-dichloro-s-triazine is employed, in place of cyanuric chloride, 2,4-difluoro-6-chloro-s-triazine or 2-fluoro-4,6-dichloro-s-triazine, as the starting material. In this case the most advantageous molar ratio of hydrogen fluoride/cyanuric halide mixture depends on the mixing ratio of the two or the three cyanuric halide components in the starting mixture. The most advantageous temperature range for the reaction when a mixture of cyanuric halides is used is the same as that when pure cyanuric chloride is employed as the starting material.

In an embodiment which is particularly advantageous industrially, the reaction according to the invention is carried out continuously by passing the reactants, in the amounts required for the desired conversion, simultaneously and continuously into the reaction space, so that the concentrations of the reactants remain constant during the period of the reaction, and continuously removing the reaction products formed from the reaction space.

The reactions are carried out in suitable reaction vessels which enable the reactants to be fed in simultaneously and continuously and the reaction products, which are present after the reaction has taken place, to be continuously withdrawn again.

Reaction vessels suitable for the reaction according to the invention are known in diverse embodiments and described in the literature(*). One example which may be mentioned is the tubular reactor in which the reactants are fed in at the same point in the tube and the reaction is brought to completion with intensive thorough mixing. The residence time of the reactants in the reactor is determined by the rate at which the reactants are fed in and the rate of withdrawal of the reaction mixture and can therefore be so regulated that the reaction proceeds with the greatest possible yield of the desired end product.

(*) See, for example, Ullmanns Encyklopëdie der tachnischen Chemie (Ullmanns Encyclopaedia of Industrial Chemistry). Verlag Chemie, Weinheim/Sergstr., 4th edition (1973), volume 3, page 321 et seq.

The residence time of the reactants in the reaction space which is necessary for the desired course of reaction is dependent on the mutual reactivity of the reactants; it can be determined by simple preliminary experiments.

According to known processes, cyanuric fluoride is prepared by reacting cyanuric chloride with inorganic fluorine compounds (for example sodium fluoride, potassium fluoride, silver fluoride, hydrogen fluoride, sulphur tetrafluoride, potassium fluorosulphite or antimony trifluoride) in the liquid phase at temperatures of −10° C. to 320° C. and under a pressure of 1 to 100 bars. The reaction is in some cases carried out in solvents or with the addition of antimony compounds as catalysts.

Compared with the known state of the art, the process of the present application is distinguished by several advantages, specifically those which follow: high yields of cyanuric fluoride are obtained with a small excess of hydrogen fluoride and, moreover, inexpensive active charcoal is employed as the catalyst. The process is suitable for a continuous course of reaction and a high specific efficiency (i.e. small apparatuses and small amounts of substance in the reactor for a high throughput) can be achieved. Because of the high toxicity of cyanuric fluoride, the latter advantage at the same time signifies a reduced safety risk. Furthermore, the only by-product obtained is hydrogen chloride, which can be further used for other purposes. The process of the present application thus also has an ecological advantage.

The fluorinated s-triazines obtained by the process of the present application are valuable intermediates which are suitable for the preparation of plant protection agents and especially for the preparation of fibre-reactive dyes.

EXAMPLE 1

Per hour, 0.5 mol of cyanuric chloride and 2.5 mols of hydrogen fluoride are passed simultaneously, at 200° C., through a heated tube reactor of 50 ml capacity which is filled with 20 g of granulated active charcoal. After passing through the reactor, the reaction gases are cooled stepwise to $-70°$ C. in order to separate off the hydrogen chloride which has formed from the other constituents. The excess hydrogen fluoride is separated off from the cyanuric fluoride formed in a distillation column which operates continuously. In a second distillation column, the cyanuric fluorides are continuously separated into pure 2,4,6-trifluoro-s-triazine and a mixture of 2,4-difluoro-6-chloro-s-triazine and 2-fluoro-4,6-dichloro-s-triazine.

Yield: 2,4,6-Trifluoro-s-triazine (cyanuric fluoride), 61 g/hour, $\sim$90% of theory (boiling point 72° C.), 2,4-Difluoro-6-chloro-s-triazine, 6 g/hour, $\sim$8% of theory, 2-Fluoro-4,6-dichloro-s-triazine, 0.5 g/hour, $\sim$0.6% of theory.

If, in the given example, corresponding amounts of 2-fluoro-4,6-dichloro-s-triazine or of 2,4-difluoro-6-chloro-s-triazine are used in place of cyanuric chloride as the starting compound, pure cyanuric fluoride is again obtained in high yield.

If, in the given example, a corresponding amount of cyanuric bromide is used in place of cyanuric chloride as the starting material, pure cyanuric fluoride is again obtained in high yield.

EXAMPLE 2

Per hour, 0.5 mol of cyanuric chloride and 2 mols of hydrogen fluoride are passed simultaneously, at 200° C., through the same reactor as in Example 1. Working up is carried out analogously to Example 1.

Yield: 2,4,6-trifluoro-s-triazine 56 g/hour, $\sim$83.0% of theory (cyanuric fluoride); 2,4-difluoro-6-chloro-s-triazine 11.5 g/hour, $\sim$15.2% of theory; 2-fluoro-4,6-dichloro-s-triazine, 1 g/hour, $\sim$1.3% of theory.

EXAMPLE 3

Per hour, 1 mol of cyanuric chloride and 5 mols of hydrogen fluoride are passed simultaneously, at 200° C., through the same reactor as in Example 1. Working up is carried out analogously to Example 1.

Yield: 2,4,6-trifluoro-s-triazine 114 g/hour, $\sim$84.4% of theory (cyanuric fluoride); 2,4-difluoro-6-chloro-s-triazine 21 g/hour, $\sim$13.9% of theory; 2-fluoro-4,6-dichloro-s-triazine 1.5 g/hour, $\sim$0.9% of theory.

EXAMPLE 4

Per hour, 0.5 mol of 2,4-difluoro-6-chloro-s-triazine and 1 mol of hydrogen fluoride are passed, at 200° C., through the same reactor as in Example 1. Working up is carried out analogously to Example 1.

Yield: 2,4,6-trifluoro-s-triazine 64 g/hour, $\sim$94.8% of theory (cyanuric fluoride); 2,4-difluoro-6-chloro-s-triazine 3 g/hour, $\sim$4.0% of theory.

EXAMPLE 5

Per hour, 0.5 mol of 2-fluoro-4,6-dichloro-s-triazine and 1.5 mols of hydrogen fluoride are passed simultaneously, at 200° C., through the same reactor as in Example 1. Working up is carried out analogously to Example 1.

Yield: 2,4,6-trifluoro-s-triazine 61.5 g/hour, $\sim$91.0% of theory (cyanuric fluoride); 2,4-difluoro-6-chloro-s-triazine 6 g/hour, $\sim$7.9% of theory.

What is claimed is:

1. In a process for the preparation of a fluorinated s-triazine, in which process a cyanuric halide containing at least one halogen other than fluoride is reacted with hydrogen fluoride, the improvement comprising carrying out said reaction in the presence of activated charcoal at a temperature between 180° C. and 220° C.

2. A process according to claim 1, which comprises carrying out the reaction in the gas phase.

3. A process according to claim 1, which comprises reacting cyanuric chloride with hydrogen fluoride in the gas phase in the presence of active charcoal.

4. A process according to claim 3, which comprises carrying out the reaction using a molar ratio of hydrogen fluoride/cyanuric chloride of 3:1 to 10:1.

5. A process according to claim 3, which comprises carrying out the reaction using a molar ratio of hydrogen fluoride/cyanuric chloride of 4:1 to 5:1.

6. A process according to claim 1, which comprises reacting 2,4-difluoro-6-chloro-s-triazine with hydrogen fluoride in the gas phase in the presence of active charcoal.

7. A process according to claim 6, which comprises carrying out the reaction using a molar ratio of hydrogen fluoride/2,4-difluoro-6-chloro-s-triazine of 1:1 to 4:1.

8. A process according to claim 6, which comprises carrying out the reaction using a molar ratio of hydrogen fluoride/2,4-difluoro-6-chloro-s-triazine of 2:1.

9. A process according to claim 1, which comprises reacting 2-fluoro-4,6-dichloro-s-triazine with hydrogen fluoride in the gas phase in the presence of active charcoal.

10. A process according to claim 9, which comprises carrying out the reaction using a molar ratio of hydrogen fluoride/2-fluoro-4,6-dichloro-s-triazine of 2:1 to 5:1.

11. A process according to claim 9, which comprises carrying out the reaction using a molar ratio of hydrogen fluoride/2-fluoro-4,6-dichloro-s-triazine of 3:1.

12. A process according to claim 1, which comprises reacting a mixture of 2,4-difluoro-6-chloro-s-triazine and 2-fluoro-4,6-dichloro-s-triazine or a mixture of cyanuric chloride, 2,4-difluoro-6-chloro-s-triazine and 2-fluoro-4,6-dichloro-s-triazine with hydrogen fluoride in the gas phase in the presence of active charcoal.

13. A process according to claim 1, which comprises carrying out the reaction continuously.

* * * * *

UNITED STATES PATENT AND TRADEMARK OFFICE
CERTIFICATE OF CORRECTION

PATENT NO. : 4,332,939

DATED : JUNE 1, 1982

INVENTOR(S) : GOTTFRIED SEIFERT, ET AL

It is certified that error appears in the above—identified patent and that said Letters Patent is hereby corrected as shown below:

Claim 1, column 4, line 23 reads:

at least one halogen other than fluoride is reacted with

Should read:

-- at least one halogen other than fluorine is reacted with --

Signed and Sealed this

Tenth Day of August 1982

[SEAL]

Attest:

Attesting Officer

GERALD J. MOSSINGHOFF

Commissioner of Patents and Trademarks